United States Patent [19]
Khorlin et al.

[11] Patent Number: 5,043,437
[45] Date of Patent: Aug. 27, 1991

[54] 5'PHOSPHONATES OF 3'-AZIDO-2',3'DIDEOXYNUCLEOSIDES

[76] Inventors: Alexandr A. Khorlin, ulitsa Generala Antonova, 7, korpus 1, kv. 131; Natalya B. Tarusova, ulitsa Zhivopisnaya, 50, kv. 40; Natalya B. Dyatkina, ulitsa Generala Antonova, 7, korpus 1, kv. 131; Alexandr A. Kraevsky, ulitsa Profsojuznaya, 132, korpus 4, kv. 111; Robert S. Bibilashvili, Kutuzovsky prospekt, 43, kv. 85; Georgy A. Galegov, ulitsa Smolnaya, 31, kv. 46, all of Moscow; Viktor M. Zhdanov, deceased, late of Moscow; by Alisa G. Bukrinskaya, administrator; by Viktor V. Zhdanov, administrator, both of Volokolamskoe shosse, 1, kv. 123, Moscow; by Dmitry J. Dergach, administrator, Begovaya ulitsa,11,kv.4, Moscow; Marina N. Korneeva, ulitsa Sakko i Vantsetti,30,kv.83, Moskovskaya blast Kaliningrad; Dmitry N. Nosik, ulitsa Miklukho-Maklaya,53,kv.99, Moscow; Svetlana N. Maiorova, Strelbischensky pereulok,26/9,kv.5, Moscow; Vadim M. Shobukhov, ulitsa Alabana,10,kv.216, Moscow, all of U.S.S.R.

[21] Appl. No.: 425,197
[22] PCT Filed: Dec. 20, 1988
[86] PCT No.: PCT/SU88/00271
§ 371 Date: Aug. 18, 1989
§ 102(e) Date: Aug. 18, 1989
[87] PCT Pub. No.: WO89/06238
PCT Pub. Date: Jul. 13, 1989

[30] Foreign Application Priority Data
Dec. 29, 1987 [SU] U.S.S.R. ............................. 4404761

[51] Int. Cl.$^5$ .................... C07H 19/00; C07H 19/20
[52] U.S. Cl. ........................................ 536/27; 536/28; 536/29

[58] Field of Search .................. 536/27-29; 514/48-49, 51-52

[56] References Cited

U.S. PATENT DOCUMENTS

| | | | |
|---|---|---|---|
| 3,524,846 | 8/1970 | Moffatt et al. | 536/29 |
| 3,560,478 | 2/1971 | Myers | 536/29 |
| 4,469,863 | 9/1984 | Ts'o et al. | 536/29 |
| 4,507,433 | 3/1985 | Miller et al. | 536/29 |
| 4,816,570 | 3/1989 | Farquhar | 536/27 |

FOREIGN PATENT DOCUMENTS 0217580  8/1987  European Pat. Off. .

OTHER PUBLICATIONS

Honjo et al., (1987), Chem. Pharm. Bull., vol. 35, No. 8, pp. 3227-3234.
Yengoyan et al. (1966), Biochemistry, vol. 5, No. 11, pp. 3629-3638.
Montgomery et al. (1978), J. Med. Chem. (1979), vol. 22, No. 1, pp. 109-112.

Primary Examiner—Johnnie R. Brown
Assistant Examiner—Gary L. Kunz
Attorney, Agent, or Firm—Burgess, Ryan & Wayne

[57] ABSTRACT

The compounds of the invention are 5'-phosphonates of 3'-azido-2',3'-dideoxynucleosides having the following general formula:

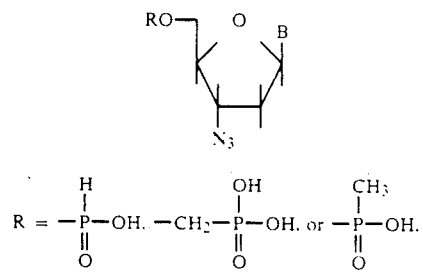

where B is thymin-1-yl, cytosin-1-yl, adenin-9-yl, or guanin-9-yl. The compounds according to the present invention are selective inhibitors of replication of the human immunodeficiency virus in a culture of human lymphocytes.

6 Claims, No Drawings

5'PHOSPHONATES OF 3'-AZIDO-2',3'DIDEOXYNUCLEOSIDES

FIELD OF THE INVENTION

The present invention relates to the art of molecular biology and, more specifically, to novel 5'-phosphonates of 3'-azido-2',3'-dideoxynucleosides which are selective inhibitors of the reproduction of the virus of human immunodeficiency in a culture of human lymphocytes.

BACKGROUND OF THE INVENTION

Known in the art are various compounds inhibiting the reproduction of the virus of human immune deficiency. The most effective among the known compounds is 3'-azido-3'-dideoxythymidine (AZT) (Mitsuya, et al, Proc. Natl. Acad. Sci., U.S.A., 1985, 82, 7096-7100; M. A. Fischl, et al, New England J. Medicine, 1987, 317, 185-191; and D. D. Richman, et al, New England J. Medicine, 1987, 317, 192-197), incorporated herein by reference.

The molecular mechanism of the effect of AZT comprises its diffusion inside cells infected with the virus of human immune deficiency. Thereafter, it is subjected to triphosphorylation and specifically blocks the synthesis of a DNA catalyzed by a reverse transcriptase which is coded by the virus of human immune deficiency. However, AZT inhibits reproduction of the virus of human immune deficiency not in all types of human cells which is apparently associated with different degrees of conversion of AZT into AZT 5'-triphosphate (AZTTP). AZT is a toxic substance which mainly affects hemopoiesis and the activity of the central nervous system.

Other 3'-azido-2',3'-dideoxynucleosides with bases: cytosine (AzC), adenine (AzA) and guanine (AzG) also exhibit an inhibiting activity in reproduction of the virus of human immune deficiency, though less clearly pronounced as compared to AZT.

SUMMARY OF THE INVENTION

The present invention is directed to novel compounds exhibiting a selective inhibition of the reproduction of the virus of human immune deficiency and which possess low toxicity.

The present compounds are 5'-phosphonates of 3'-azido-2',3'-dideoxynucleosides having the formula

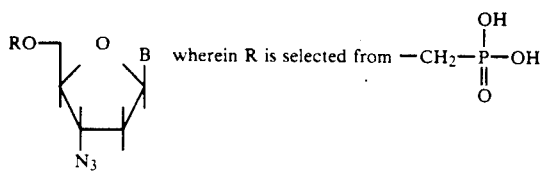 wherein R is selected from $-CH_2-\overset{\overset{\displaystyle OH}{|}}{\underset{\underset{\displaystyle O}{\|}}{P}}-OH$ and B is selected from

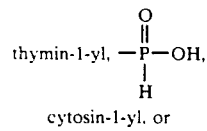

thymin-1-yl, $-\overset{\overset{\displaystyle O}{\|}}{\underset{\underset{\displaystyle H}{|}}{P}}-OH$, cytosin-1-yl, or adenin-9-yl, or guanin-9-yl, $-\overset{\overset{\displaystyle O}{\|}}{\underset{\underset{\displaystyle CH_3}{|}}{P}}-OH$ These compounds are capable of inhibiting the reproduction of the human immune deficiency virus and are less toxic as compared to the prior art compounds.

DETAILED DESCRIPTION OF THE INVENTION

The compounds according to the present invention are white amorphous powders, readily soluble in water, sparingly soluble in ethanol and insoluble in other organic solvents.

The purity and structure of the compounds according to the present invention were proven by chromatography, UV- and NMR-spectroscopy.

The compounds according to the present invention selectively inhibit the virus of human immune deficiency in vitro in a culture of human lymph cytes H9/IIIB MT4.

As the source of the virus of human immune deficiency use was made of grafted lymphoblastoidal lines of human cells producing said virus (H9/IIIB and MT4), the production of the virus by the cells was controlled in an immunofluorescence reaction and by means of electron microscopy. Cells were cultured in RPMI 1640 with a 15% inactivated serum of cow embryos with 300 μg/ml of glutamine, 100 μg/ml of gentamycin, 10 mM of HEPES-buffer and grown as a suspension. The cultured liquid was collected by centrifugation at 5,000 r.p.m. for 10 minutes and lymphocytes of the peripheral blood of healthy donors were used for infecting at the rate of 1 ml of a supernatant of a cultured liquid containing the virus of human immune deficiency per every $10^6$ lymphocytes of human peripheral blood isolated from the harinized blood of healthy donors in a phycoll-isopane gradient. The cells were cultures in RPMI 1640 with a 15% inactivated serum of cow embryos, 300 μg/ml of glutamine, 100 μg/ml of gentamycin, 100 mM of HEPES-buffer and incubated for 48 hours at 37° C. in a humidified $CO_2$ atmosphere in the presence of phytohemagglutinin at the concentration of 100 μg/ml. A further culturing of lymphocytes after the incorporation of the virus was effected for 6 days in the presence of a 10% natural human lymphocytic interleukin-2.

The determination of an antigenic effect (immunoenzymatic analysis) of the material was carried out in 96-hole plastic plates by a conventional technique. The indirect immunofluorescence reaction was carried out in fixed preparations of antigen containing cells producing the virus of human immune deficiency. The calculation of the viable cells was effected with the use of trypan blue dye.

The results of the tests are shown in Tables 1-4 hereinbelow.

As the control use was made of azidonucleosides AZT, AzC, AzA and AzC, respectively.

TABLE 1

INHIBITION OF HUMAN IMMUNO-DEFICIENCY VIRUS (HIV-1) WITH 5'-PHOSPHONATES OF 3'-AZIDO-2',3'-DIDEOXY THHMIDINE INH9/IIIB CELLS

| | | COMPOUNDS OF THE INVENTION | | | | | | | | CONTROL | | |
|---|---|---|---|---|---|---|---|---|---|---|---|---|
| | | 5'-methylenephosphonate of AZT | | | 5'-hydrogenphosphonate of AZT | | | 5'-methylphosphonate of AZT | | | 3'-azido-2',3'-dideoxythymidine (AZT) | |
| | | | $(C + V)^{**}$ | | | C + V | | | C + V | | | C + V |
| No. | Experiment Conditions | $(C \times 10^6)$ (a) | $\times 10^6$ (b) | % (b) ÷ (a) | $C \times 10^6$ (c) | $\times 10^6$ (d) | % (d) ÷ (c) | $C \times 10^6$ (e) | $\times 10^6$ (f) | % (f) ÷ (e) | $C \times 10^6$ (g) | $\times 10^6$ (h) | % (h) ÷ (g) |
| 1. | Cells (control) | 1.10 | — | — | 1.20 | — | — | 1.10 | — | — | 1.20 | — | — |
| 2. | Cells + Virus | 1.00 | 0.52 | 52 | 0.60 | 0.21 | 36 | 1.00 | 0.52 | 52 | 0.60 | 0.28 | 46 |
| 3. | Cells + Virus + Compound (1 μM) | 0.75 | 0.11 | 15 | 0.65 | 0.12 | 18 | 1.20 | 0.26 | 22 | 0.60 | 0.06 | 10 |
| 4. | Cells + Virus + Compound (5 μM) | — | — | — | 0.60 | 0.13 | 22 | — | — | — | 0.58 | 0.06 | 11 |
| 5. | Cells + Virus + Compound (10 μM) | 1.00 | 0.06 | 6 | 1.00 | 0.14 | 14 | 0.75 | 0.13 | 17 | 0.35 | 0.035 | 10 |

*C = Concentration of living cells per ml.
**(C + V) = Concentration of virus-containing cells (per ml and percentage of virus containing cells to the living cells).

The data in Table 1 demonstrates that at effective concentrations of phosphonate derivatives of AZT, the quantity of living cells is significantly higher than in the case of AZT. For 5'-methylenephosphonate and 5-hydrogenphosphonate of AZT, the quantity is close to control ($C \times 10^6$ is in both cases $1.0 \times 10^6$, for AZT $-0.35 \times 10^6$). Thus, the toxicity of these two components is much lower than for AZT by the retention of inhibitory activity of virus reproduction.

TABLE 2

INHIBITION OF HUMAN IMMUNODEFICIENCY VIRUS REPRODUCTION WITH 5'-HYDROGENPHOSPHONATES OF 3'-AZIDO-2',3'-DIDEOXYCYTIDINE IN MT4 CELLS

| | | Compounds of this Invention | | | Control | | |
|---|---|---|---|---|---|---|---|
| | | 5'-hydrogenphosphonate of AzC | | | AzC | | |
| | | | $(C + V)^{**}$ | | | C + V | |
| No. | Experiment Conditions | $^*C \times 10^6$ (i) | $\times 10^6$ (j) | % (j) ÷ (i) | $C \times 10^6$ (k) | $\times 10^6$ (l) | % (l) ÷ (k) |
| 1. | Cells (Control) | 1.03 | — | — | 1.03 | — | — |
| 2. | Cells + Virus | 0.42 | 0.42 | 100 | 0.42 | 0.42 | 100 |
| 3. | Cells + Virus + Compound (10 μM) | 0.52 | 0.48 | 92 | 0.46 | 0.45 | 97 |
| 4. | Cells + Virus + Compound (30 μM) | 0.73 | 0.57 | 78 | 0.40 | 0.36 | 91 |

*C = Concentration of living cells per ml.
**(C + V) = Concentration of virus-containing cells (per ml and percentage of virus-containing cells to the living cells).

TABLE 3

INHIBITION OF HUMAN IMMUNODEFICIENCY VIRUS REPRODUCTION WITH 5'-PHOSPHONATES OF 3'-AZIDO-2',3'-DIDEOXYADENOSINE IN MT4 CELLS

| | | Compounds of this Invention | | | | | | | | Control | | |
|---|---|---|---|---|---|---|---|---|---|---|---|---|
| | | 5'-methylenephosphonate of AzA | | | 5-hydrogenphosphonate of AzA | | | 5'-methylphosphonate of AzA | | | AzA | |
| | | | $(C + V)^{**}$ | | $C \times 10^6$ | C + V | | | C + V | | $C \times 10^6$ | C + V | |
| NO. | Experiment conditions | $C^* \times 10^6$ (M) | $\times 10^6$ (N) | % (N) ÷ (M) | (O) | $\times 10^6$ (P) | % (P) ÷ (O) | $C \times 10^6$ (Q) | $\times 10^6$ (R) | % (R) ÷ (Q) | (S) | $\times 10^6$ (T) | % (T) ÷ (S) |
| 1. | Cells (control) | 0.95 | — | — | 0.95 | — | — | 0.95 | — | — | 0.95 | — | — |
| 2. | Cells + virus | 0.48 | 0.46 | 96 | 0.48 | 0.46 | 96 | 0.48 | 0.46 | 96 | 0.48 | 0.46 | 96 |
| 3. | Cells + virus + Compound | 0.48 | 0.29 | 61 | 0.56 | 0.36 | 65 | 0.51 | 0.45 | 88 | 0.45 | 0.42 | 92 |

TABLE 3-continued
INHIBITION OF HUMAN IMMUNODEFICIENCY VIRUS REPRODUCTION WITH 5'-PHOSPHONATES OF 3'-AZIDO-2',3'-DIDEOXYADENOSINE IN MT4 CELLS

| | | Compounds of this Invention | | | | | | | | | | | |
|---|---|---|---|---|---|---|---|---|---|---|---|---|---|
| | | 5'-methylenephosphonate of AzA | | | 5-hydrogenphosphonate of AzA | | | 5'-methylphosphonate of AzA | | | Control AzA | | |
| | | | | (C + V)** | $C \times 10^6$ (O) | | C + V | $C \times 10^6$ (Q) | | C + V | $C \times 10^6$ (S) | | C + V |
| NO. | Experiment conditions | $C^* \times 10^6$ (M) | $\times 10^6$ (N) | % (N) ÷ (M) | | $\times 10^6$ (P) | % (P) ÷ (O) | | $\times 10^6$ (R) | % (R) ÷ (Q) | | $\times 10^6$ (T) | % (T) ÷ (S) |
| 4. | Cells + virus + Compound (5 μM) | 0.65 | 0.35 | 56 | 0.62 | 0.40 | 65 | 0.58 | 0.47 | 81 | 0.52 | 0.45 | 86 |
| 5. | Cells + virus + Compound (10 μM) (30 μM) | 0.94 | 0.30 | 32 | 0.92 | 0.35 | 38 | 0.61 | 0.41 | 67 | 0.56 | 0.45 | 80 |

***C and C + V are as defined in Tables 1 and 2.
In Table 3, the effect of virus inhibition with 5'-methylenephosphonate and 5'-hydrogenphosphate of AzA is close to that of AzA. The toxicity of the compounds of the invention are lower than that of AzA as shown by concentration of living cells on the administration of 30 μm of each of the compounds (cf. 0.94 × 10⁶ and 0.92 × 10⁶ against 0.56 × 10⁶ for AzA).

TABLE 4
INHIBITION OF HUMAN IMMUNODEFICIENCY VIRUS WITH 5'-PHOSPHONATES OF 3'-AZIDO-2',3'-DIDEOXYGUANOSINE IN MT4 CELLS

| | | Compounds of this Invention | | | | | | | | | | | |
|---|---|---|---|---|---|---|---|---|---|---|---|---|---|
| | | 5'methylenephosphonate of AzG | | | 5'-Hydrogenphosphonate of AzG | | | 5'methylphosphonate of AzG | | | Control AzG | | |
| | | | | (C + V)** | $C \times 10^6$ (W) | | C + V | $C \times 10^6$ (Y) | | C + V | $C \times 10^6$ (AA) | | C + V |
| NO. | Experiment conditions | $C^* \times 10^6$ (U) | $\times 10^6$ (V) | % (V) ÷ (U) | | $\times 10^6$ (X) | % (X) ÷ (W) | | $\times 10^6$ (Z) | % (Z) ÷ (Y) | | $\times 10^6$ (BB) | % (BB) ÷ (AA) |
| 1. | Cells (control) | 1.2 | — | — | 1.2 | — | — | 1.2 | — | — | 1.2 | — | — |
| 2. | Cells + virus | 0.65 | 0.65 | 100 | 0.65 | 0.65 | 100 | 0.65 | 0.65 | 100 | 0.65 | 0.65 | 100 |
| 3. | Cells + virus + compound (1 μM) | 0.68 | 0.62 | 91 | 0.62 | 0.60 | 96 | 0.65 | 0.65 | 100 | 0.65 | 0.63 | 96 |
| 4. | Cells + virus + compound (5 μM) | 0.70 | 0.48 | 68 | 0.75 | 0.21 | 28 | 0.70 | 0.43 | 61 | 0.71 | 0.68 | 96 |
| 5. | Cells + virus + compound (10 μM) | 0.85 | 0.26 | 30 | 0.86 | 0.20 | 23 | 0.78 | 0.45 | 58 | 0.76 | 0.73 | 96 |
| 6. | Cells + virus + compound (30 μM) | 1.04 | 0.13 | 12 | 1.07 | 0.11 | 10 | 0.56 | 0.38 | 68 | 0.81 | 0.73 | 90 |

***C and C + V are as defined in Tables 1 and 2.

As seen from the results shown in Tables 1-4, in all cases, the compounds according to the present invention, namely 5'-methylenephosphonates or 5'-hydrophosphonates of 3'-azido-2',3'-dideoxynucleosides are effective in inhibiting reproduction of the virus of human immunedeficiency, while suppressing the reproduction of cells to a much lower extent than the corresponding azidonucleosides. While having a satisfactory effect on the virus, the compounds according to the present invention, viz. 5'-methylphosphonates of 3'-azido-2',3'-dideoxynucleosides, cause per se a considerable inhibition of cell growth due to their toxicity which results in a reduced cell population in comparison with 5'-methylenephosphonates or 5'-hydrophosphonates of 3'-azido-2',3'-dideoxynucleo-sides.

Therefore, all the compounds according to the present invention show a clearly pronounced inhibitory effect on the virus of human immune deficiency.

The compounds according to the present invention were tested for toxicity. The test results are shown in Table 5 hereinbelow wherefrom it is clear that the present compounds exhibit lower toxicity as compared to the starting azidonucleosides (AZT, AzC, AzA, AzG).

TABLE 5
TOXICITY OF THE COMPOUNDS ACCORDING TO THE PRESENT INVENTION IN COMPARISON WITH AZIDONUCLEOSIDES IN CULTURES OF HUMAN LYMPHOCYTES H9/IIIB and MT4

| | | Growth Inhibition at the Concentration of 0.5 mM, % | |
|---|---|---|---|
| No. | Compound | H9. IIIB | MT4 |
| 1. | 5'-methylenephosphonate of 3'-azido-2',3'-dideoxythymidine | 35 | 10 |
| 2. | 5'-methylenephosphonate of 3'-azido-2',3'-dideoxycytidine | 20 | 65 |

TABLE 5-continued

TOXICITY OF THE COMPOUNDS ACCORDING TO
THE PRESENT INVENTION IN COMPARISON WITH
AZIDONUCLEOSIDES IN CULTURES OF HUMAN
LYMPHOCYTES H9/IIIB and MT4

| No. | Compound | Growth Inhibition at the Concentration of 0.5 mM, % | |
|---|---|---|---|
| | | H9/IIIB | MT4 |
| 3. | 5'-methylenephosphonate of 3'-azido-2',3'-dideoxyadenosine | 10 | 30 |
| 4. | 5'-methylenephosphonate of 3'-azido-2',3'-dideoxyguanosine | 30 | 65 |
| 5. | 5'-hydrophosphonate of 3'-azido-2',3'-dideoxythymidine | 10 | 30 |
| 6. | 5'-hydrophosphonate of 3'-azido-2',3'-dideoxycytidine | 10 | 10 |
| 7. | 5'-hydrophosphonate of 3'-azido-2',3'-dideoxyadenosine | 10 | 0 |
| 8. | 5'-hydrophosphonate of 3'-azido-2',3'-dideoxyguanosine | 20 | 30 |
| 9. | 5'-methylphosphonate of 3'-azido-2',3'-dideoxythymidine | 85 | 100 |
| 10. | 5'-methylphosphonate of 3'-azido-2',3'-dideoxycytidine | 85 | 100 |
| 11. | 5'-methylphosphonate of 3'-azido-2',3'-dideoxyadenosine | 70 | 80 |
| 12. | 5'-methylphosphonate of 3'-azido-2',3'-dideoxyguanosine | 80 | 100 |
| 13. | AZT | 100 | 100 |
| 14. | AzC | 80 | 60 |
| 15. | AzA | 70 | 80 |
| 16. | AzG | 90 | 100 |

The compounds according to the present invention are prepared in the following manner.

5'-methylenephosphonates of 3'-azido-2',3'-dideoxynucleosides are prepared by reacting hydromethylphosphonic acid P,P-diethyl ether toluenesulphonate with an azidonucleoside or with an N-protected azidonucleoside derivative treated with sodium hydride in an organic solvent in an atmosphere of an inert gas. Then, the desired product is recovered from the reaction mass and purified. The desired product yield is within the range of from 25 to 40% by weight.

5-hydrophosphonates of 3'-azido-2',3'-dideoxynucleosides are prepared by reacting imidazole, phosphorus trichloride and an azidonucleoside or an N-protected azidonucleoside derivative in an organic solvent, followed by the recovery and purification of the desired product. The yield of the desired product is equal to 58–80% by weight.

5'-methylphosphonates of 3'-azido-2',3'-dideoxynucleosides are obtained by reacting dichloromethylphosphonate with an azidonucleoside or with an N-protected azidonucleoside derivative in an organic solvent, followed by isolation and purification of the desired product. The yield of the desired product is equal to 30–40% by weight.

For a better understanding of the present invention, some specific examples illustrating the preparation of the compounds of the present invention are given hereinbelow.

EXAMPLE 1

To a suspension of sodium hydride (54 mg, 2.25 mmol) in 3 ml of dimethylformamide, a solution of 3'-azido-2',3'-dideoxythymidine (200 mg, 0.75 mmol) in 5 ml of dimethylformamide was added for 15–20 minutes in an inert gas atmosphere and stirred for 30 minutes at the temperature of 20° C. A solution of hydroxymethylphosphonic acid P,P-diethyl ether toluenesulfonate (240 mg, 0.75 mmol) in 3 ml of dimethylformamide was then added to the reaction mass and the latter was vigorously stirred for 3 days at 20° C. The progress of the reaction was controlled by way of thin-layer chromatography in a chloroform-ethanol 9:1 (A) system. On completion of the reaction 0.13 ml of acetic acid was added, the reaction mass was evaporated and re-evaporated with 5 ml of dimethylformamide. The residue was extracted with chloroform (5×5 ml). The extracts were evaporated and the residue was purified in a column with silica gel 40/100μ (12×2.5 cm). The elution was carried out with 300 ml of chloroform, then with 400 ml of a chloroform-ethanol (9:1) mixture followed by collecting fractions of 2 ml. The respective fractions were combined and evaporated to give 130 mg of an oily substance with $R_f=0.63$ (system A) which was dissolved in 3 ml of dimethylformamide, added to trimethylsilylbromine (0.3 ml) at 4° C., stirred for 30 minutes and allowed to stay for another 24 hours at 20° C. The reaction mass was evaporated, added to 5 ml of water and triethylamine to a pH=9.0, allowed to stay for one hour and extracted with chloroform (3×5 ml). The aqueous layer was evaporated, the residue was purified in a column with 300 ml of DEAE cellulose (in the $HCO_3^-$ form) with a linear gradient of ammonium bicarbonate of from 0 to 3.3M. The total volume of the resulting eluent was 3l. The fractions containing the desired product were evaporated, re-evaporated with water (5×10 ml) and ethanol (3×20 ml). The residue was extracted with 10 ml of methanol, evaporated to 2 ml, added to 30 mg of $NaClO_4$ and 5 ml of acetone. The residue was separated, washed with acetone and dried. There were obtained 82 mg (40% by weight) of 5'-methylene phosphonate of 3'-azido-2',3'-dideoxythymidine comprising a white amorphous compound insoluble in organic solvents with $R_f=0.2$, system isopropanol-ammonia-water 7:1:2 (B); (highly effective liquid chromatography on nucleosyl 120-7 $NH_2$ in a linear gradient of $K_2HPO_4$ 0.5–1M), retention time 10.6 min. UV-spectrum, nm, $\lambda_{max}$ 265 (ε9600 pHI), $\lambda_{min}$ 238 (ε3500 pHI); H-NMR ($D_2O$, δ, ppm): 7.54, d (1H, H6, J=0.5 Hz); 1.95, d (3H, $CH_3$, J=0.5 Hz); 6.18, t, (1H, HI', $J_{I'2'}=6.0$ Hz); 2.60, m, (2H, 2H2'); 3.70–4.80, m. (4H,H3'+H4'+2H5'); 3.68, d, (2H, $CH_2P$, $J_{PH}=8.6$ Hz). $^{31}$P-NMR ($D_2O$, δ, ppm): 15.7, t. ($J_{P,H}=8.6$ Hz).

EXAMPLE 2

To a suspension of sodium hydride (54 mg, 2.25 mmol) in 3 ml of dimethylformamide, a solution of 3'-azido-2',3'-dideoxy-N-benzoylcytidine (265 mg, 0.75 mmol) in 5 ml of dimethylformamide was added for 15–20 minutes in an inert gas atmosphere and stirred for 30 minutes at the temperature of 20° C. A solution of hydroxymethylphosphonic acid P,P-diethyl ether toluenesulfonate (240 mg, 0.75 mmol) in 3 ml of dimethylformamide was then added and the reaction mass was vigorously stirred for 3 days at 20° C. The progress of the reaction was controlled by thin-layer chromatography in the system A. On completion of the reaction 0.13 ml of acetic acid was added, and the reaction mass was evaporated. The residue was extracted with chloroform (5×5 ml) and the chloroform was then evaporated. The residue was dissolved in 3 ml of dimethylformamide, added to 0.3 ml of trimethylsilylbromide at 4° C. The solution was allowed to stay for 24 hours at 20° C. The reaction mass was evaporated, added to 5 ml of water and triethylamine to a pH of 9.0 and extracted with chloroform after 1 hour. The aqueous layer was concentrated to 1 ml and added to 30 ml of unsaturated solution of ammonia in methanol to remove the N-benzoyl group. After 24 hours, the solution was evaporated.

The recovery and purification of the desired product were carried out in a manner similar to that described in Example 1 to give 5'-methylenephosphonate of 3'-azido-2',3'-dideoxycytidine. The product yield was 45% by weight.

The resultant compound was a white amorphous substance well-soluble in water and insoluble in organic solvents.

$R_f=0.24$ (B); retention time 8.8 minutes. UV-spectrum, nm, pH=7.); $\lambda_{max}$ 271 ($\epsilon$8900); $\lambda_{min}$ 252 ($\epsilon$6300).
$^1$H-NMR (D$_2$O, $\delta$, ppm): 7.66, d, (1H, H5, $J_{5,6}$=8.0=8.0 Hz); 5.79, d, (1H, H5, $J_{5,6}$-8.0 Hz); 5.95 t, (1H, HI', $J_{1',2'}$=6.0 Hz); 2.66 m (2H, 2H2'); 3.81-4.34 m (4H, H3'H4'+2H5'); 3.75 d (2H, CH$_2$P, $J_{p,H}$=8.6 Hz). $^{31}$P-NMR (D$_2$O, $\delta$, ppm): 16.0 5, $J_{P,H}$=8.6 Hz.

EXAMPLE 3

In a manner similar to that described in Example 2, 5'-methylenephosphonate of 3'-azido-2',3'-dideoxyadenosine was obtained. The yield was 35% by weight.

The resultant compound was a white amorphous substance, well-soluble in water and insoluble in organic solvents; $R_f$0.12 (B), the retention time was 12,4 minutes. UV-spectrum, nm, pH 7.0:$\lambda_{max}$ 261 ($\epsilon$15100)$\lambda_{min}$ 231 ($\epsilon$2750); $^1$H-NMR (D$_2$O, $\delta$, ppm): 8.23 s (IH, H2); 8.38 s (1H, H8); 640 t (1H H1'; $J_{1,2}$=5.0 Hz); 2.80 m (2H, 2h2); 4.00-4.50 m (4H, H3+H4+2H5); 3.70 d (2H, CH$_2$P, $J_{P,H}$=8.6 Hz). $^{31}$P-NMR (D$_2$O, $\delta$, ppm): 1.57, 5, $J_{P,H}$=8.6 Hz.

EXAMPLE 4

In a manner similar to that described in Example 2, 5'-methylenephosphonate of 3'-azido-2',3'-dideoxyguanosine was obtained. The yield was 27% by weight.

The resultant compound was a white amorphous substance, well-soluble in water and insoluble in organic solvents.

$R_f$=0.08 (B), retention time 12.3 minutes. UV-spectrum, nm, pH 7.0: $\lambda_{max}$ 253 ($\epsilon$11500), $\lambda_{mun}$ 227 ($\epsilon$2900); $^1$H-NMR (D$_2$O, $\delta$, ppm): 8.10 s (1H,H8); 6.35 ; t (IH,HI', $J_{1',2'}$=5.0 Hz; 2.8 m (2H, 2H2'); 3.95-4.40 m (4H, H3'+H4'+2H5'); 3.65 d (2H, CH$_2$P, $J_{P,H}$=8.6 Hz). $^{31}$P-NMR (D$_2$O, $\delta$, ppm): 15.8 t, $J_{P,H}$=8.6 Hz).

EXAMPLE 5

Imidazole (0.50 g, 7.36 mmol) was dissolved in 15 ml of absolute acetonitrile and cooled to 0° C. Phosphorus trichloride (0.19 ml, 2.16 mmol) was added under stirring. The reaction mixture was stirred for 15 minutes at 0° C., a solution of 3'-azido-2',3'-dideoxythymidine (134 mg, 0.5 mmol) in 10 ml of acetone was then added dropwise for 30 minutes so that the reaction mass temperature did not rise above +5° C. The reaction mass was stirred for 2 hours at 20° C., added to 3.5 ml of water and evaporated over 30 minutes. Then the compound was placed into a column with Toepearl DEAE (5×25 cm) and eluted with ammonium bicarbonate with a linear gradient of concentrations of from 0 to 0.3M. The total volume wa 1 liter. The fractions containing the desired product were collected and evaporated. The excess of the salt was removed by way of a repeated reevaporation with water. The residue was lyophilized from water to give 140 mg of 5'-hydrophosphonate of 3'-azido-2',3'-dideoxythymidine (80% by weight) comprising a while amorphous substance, well soluble in water and sparingly soluble in ethanol.

$R_f$=0.55 (B), retention time 7.2 minutes; UV-spectrum, nm, pHI: $\lambda_{max}$ 265 ($\epsilon$9800), $\lambda_{min}$ 238 ($\epsilon$3400). $^1$H-NMR (D$_2$O, $\delta$, ppm): 7.52 d (IH, H6, J==0.5 Hz); 1.92 d (3H, CH$_3$, J=0.5 Hz) 6,52 t (IH, HI', $J_{r,2'}$=6.0 Hz); 2.45 m (2H, 2H2'); 3.90-4.42 m (4H, H3+H4'+2H5'); 6.64 d (IH, H$^p$, $J_{P,H}$=6.29 Hz). $^{31}$P-NMR (D$_2$O, $\delta$, ppm): 6.6 m ($J_{P,H}$=629 Hz, $J_{P,H}5'$=6.3 Hz, $J_{P,H}4$=1.6 Hz) (the spectrum was taken without inhibition of splitting on protons).

EXAMPLE 6

Imidazole (0.50 g, 7.36 mmol) was dissolved in 15 ml of absolute acetonitrile and cooled to 0° C. Phosphorus trichloride (0.19 ml, 2.16 mmol) and then triethylamine (1.05 ml, 7.54 mmol) were added under stirring. The reaction mixture was stirred for 15 minutes at 0° C., and then a solution of 3'-azido-2',3'-dideoxy-N-benzoylcytidine (182 mg, 0.5 mmol) in 10 ml of acetonitrile was added dropwise for 30 minutes so that the reaction mass temperature did not rise above 5° C. The reaction mass was stirred for 2 hours at 20° C., added to 3.5 ml of water and evaporated after 30 minutes. The removal of the benzoyl group was effected using a saturated solution of ammonia in methanol at 20° C. for 24 hours. The recovery and purification were conducted following the procedure similar to that described in Example 5.

There was thus obtained 5'-hydrophosphonate of 3'-azido-2',3'-dideoxycytidine (the yield was 72% by weight). The resultant compound was a white amorphous substance, well-soluble in water and sparingly soluble in ethanol. $R_f$=0.50 (B), the retention time 5.1 min.

UV-spectrum, nm, pH 7.0: $\lambda_{max}$ 273 ($\epsilon$8750), $\lambda_{min}$ 248 ($\epsilon$6200); $^1$H-NMR (D$_2$O, $\delta$, ppm): 7.26 d (IH, H6, $J_{5,6}$=8.0 Hz); 5.78 d (IH,H5 $J_{5,6}$=8.0 Hz); 5.95 t (IH,HI', $J_{1',2'}$=6.0 Hz); 2.70 m (2H, 2H2'); 3.75-4.32 m (4H, H3'+H4'+2H5'); 6.63 d (IH,H$^p$, $J_{P,H}$=632 Hz). $^{31}$P-NMR (D$_2$O, $\delta$, ppm); 6.6 m ($J_{P,H}$=632 Hz, $J_{P,H}5'$==6.3 Hz), $J_{P,H}4'$=1.6 Hz.

EXAMPLE 7

In a manner similar to that dsscribed in Example 6, 5'-hydrophosphonate of 3'-azido-2',3'-dideoxyadenosine was obtained (yield=67% by weight).

The resultant compound was a white amorphous substance, well-soluble in water and sparingly soluble in ethanol.

$R_f$=0.489 (B); retention time 8.9 min; UV-spectrum, nm, pH 7.0: $\lambda_{max}$ 260 ($\epsilon$15350), $\lambda_{min}$ (229 ($\epsilon$2700); $^1$H-NMR (D$_2$O, $\delta$, ppm): 8.39 s ($^1$H,H8); 8.25 s (IH,H2), 6.40 t (IH, H', $J_{1,2}$=5.0 Hz); 2.80 m (2H, 2H2'), 4.04-4.60 m (4H, H3'+H4'+2H5'); 6.65 d (1H,H$^p$, $J_{P,H}$==632 Hz). The $^{31}$P-NMR spectrum was similar to that of the compound obtained in Example 7.

EXAMPLE 8

5-hydrophosphonate of 3'-azido-2',3'-dideoxyguanosine was obtained in a manner similar to that described in Example 6. The yield was 58% by weight. The resultant compound was a white amorphous substance, well-soluble in water and sparingly soluble in ethanol.

$R_f=0.44$ (B), retention time as 8.4 minutes. UV-spectrum, nm, (pH=7.0): $\lambda_{max}$ 252 ($\epsilon$11500), $\lambda_{min}$ 226 ($\epsilon$3000); $^1$H-NMR (D$_2$O, $\delta$, ppm): 8.08 s (IH,H8); 6.42 t (1H, HI', $J_{1',2'}=5.0$ Hz); 2.80 m (2H, 2H2'), 4.00–4.40 m (4H, H3'+H4'+2H5'); 6.63 d (1H,H$^p$, $J_{P,H}=654$ Hz). $^{31}$P-NMR (D$_2$O, $\delta$, ppm): 6.6 m ($J_{P,H}=654$ Hz, $J_{P,H}5'=6.4$ Hz, $J_{P,H}4'=1.5$ Hz).

EXAMPLE 9

To a solution of 3'-azido-2',3'-dideoxythymidine (130 mg, 0.5 mmol) in 2 ml of trimethylphosphate at 0° to ° C. dichloromethanephosphate (200 mg, 1.5 mmol) was added for 3 hours, stirred overnight at +4° C., and for 5 hours at 20° C. The reaction mass was evaporated, the residue was added to 5 ml of water and 1 ml of triethylamine upon cooling to 0° C., and allowed to stay for 1 hour and again evaporated. The residue was purified by chromatography on a column (20×4 cm) with DEAE cellulose in HCO$_3-$. The elution was conducted using 3l of ammonium bicarbonate with a linear gradient of from 0 to 0.1M. The fractions containing the desired product were evaporated. The salt excess was removed by repeated and re-evaporation with water. The residue was extracted with 10 ml of methanol, concentrated to 2 ml, added to 30 mg of NaClO$_4$ and 5 ml of acetone. The residue was separated, washed with acetone and dried. There were thus obtained 120 mg (33.0% by weight) of 5'-methylphosphonate of 3'-azido-2',3'-dideoxythymidine comprising a white amorphous substance, well-soluble in water and sparingly soluble in ethanol.

$R_f=0.6$ (B); retention time 7.0 min, UV-spectrum, nm pH 1.0; $\lambda_{max}$ 265 ($\epsilon$9600), $\lambda_{min}$ 240 ()$\epsilon$3450); $^1$H-NMR (D$_2$O, $\delta$, ppm): 7.60 d (1H, H6, J=0.5 Hz); 1.88 d (3H, CH$_3$, J=0.5 Hz) 6.16 t (IH,HI', $J_{1',2'}=6.0$ Hz); 2.46 m (2H, 2H2'); $J_{P,CH_3}=3.80-4.90$ m (4H, H3'+H4'+2H5'); 1.30 d (3H, CH$_3$P, $J_{P,CH_3}=17$ Hz)

EXAMPLE 10

To a solution of 3'-azido-2',3'-dideoxy-N-benzoyl-cytidine (187 mg, 0.5 mmol) in 2 ml of trimethylphosphate at from 0° to 4° C., dichloromethanephosphonate (200 mg, 1.5 mmol) was added for 3 hours, stirred overnight at 4° C. and for 5 hours at 20° C. The reaction mass was evaporated, the residue was added to 5 ml of water and 1 ml of triethylamine upon cooling to 0° C., and allowed to stay for 1 hour and evaporated. For the removal of the N-benzoyl group the residue was added to 25 ml of a saturated solution of ammonium in methanol. 24 hours thereafter, the solution was evaporated to dryness. The recovery and purification were conducted following a procedure similar to that described in Example 9.

There was obtained 5'-methylphosphonate of 3'-azido-2',3'-dideoxycytidine in the yield of 35% by weight. The resultant compound was a white amorphous substance well soluble in water.

$R_f=0.48$ (B) retention time 4.6 minutes; UV-spectrum,nm, pH=7.0: $\lambda_{max}=271$ ($\epsilon$8800), $\lambda_{min}$ 250 ($\epsilon$6400). $^1$H-NMR (D$_2$O, $\delta$, ppm): 7.65 d (1H,H6, $J_{5,6}=8.0$ Hz); 5.80 d (IH, H5, $J_{5,6}=8.0$ Hz); 5.97 t (1H, HI', $J_{1',2'}=6.0$ Hz), 2.70 m (2H, 2H2'), 3.78–4.34 m (H3'+H4'+2H5'); 1.30 d (3H, CH$_3$P $J_{P,CH_3}=17$ Hz).

EXAMPLE 11

5'-methylphosphonate of 3'-azido-2',3'-dideoxyadenosine was obtained in a manner similar to that described in Example 10. The yield was 30% by weight. The resultant compound was a white amorphous substance, well soluble in water.

$R_f=0.38$ (B); retention time 7.8 minutes. UV-spectrum, nm, pH 7.0: $\lambda_{max}$ 260 ($\epsilon$15300), $\lambda_{min}$ 230 ($\epsilon$2300); H-NMR (D$_2$O, $\delta$, ppm): 8.24 s (IH, H8); 6.40 t (IH, HI, $J_{1,2}=5.0$ Hz) 2.80 m (2H, 2H2'); 4.00–4.40 m (4H, H3'+H4'+2H5'); 1.30 d (3H, CH$_3$P, $J_{P,CH_3}=17$ Hz).

EXAMPLE 12

5'-methylphosphonate of 3'-azido-2',3'-dideoxyguanosine was obtained in a manner similar to that described in Example 11. The yield was 30% by weight. The resultant compound was a white amorphous compound, well soluble in water.

$R_f=0.55$ (B); retention time 7.6 min. UV-spectrum, nm, pH=7.0: $\lambda_{max}$ 253 ($\epsilon$11000), $\lambda_{min}$ 228 ($\epsilon$2800). H-NMR (D$_2$O, $\delta$, ppm): 8.08 s (1H, H8); 4.00–4.40 m (4H, H3'+H4'+2H5'); 1.30 d (3H, CH$_3$P, $J_{P, CH_3}=17$ Hz).

Industrial Applicability

The compounds according to the present invention, viz. 5'-phosphonates of 3'-azido-2',3473 -dideoxynucleosides are capable of inhibiting the reproduction of the virus of human immune deficiency in a culture of lymphocytes and can be useful in medicine.

We claim:

1. 5'-Phosphonates of 3'-azido-2',3'-dideoxynucleosides of the formula:

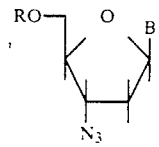

wherein R is a phosponate selected from the group consisting of

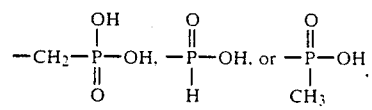

and B is thymin-1-yl, cytosin-1-yl, adenin-9-yl or guanin-9-yl.

2. The compound of claim 1, wherein R is

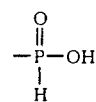

and B is thymin-1-yl.

3. The compound of claim 1, wherein R is

and B is adenin-9-yl.
4. The compound of claim 1, wherein R is
and B is guanin-9-yl.
5. The compound of claim 1, wherein R is
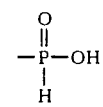
and B is cytosin-1-yl.
6. The compound of claim 1, wherein R is
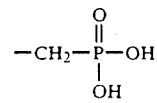
and B is thymin-1-yl.
* * * * *